(12) United States Patent
Melbouci

(10) Patent No.: US 8,450,386 B2
(45) Date of Patent: May 28, 2013

(54) USE OF POLYETHYLENE GLYCOL BASED FLUIDIZED POLYMER SUSPENSION IN FUNCTIONAL SYSTEMS

(75) Inventor: Mohand Melbouci, Wilmington, DE (US)

(73) Assignee: Hercules Incorporated, Wilmington, DE (US)

( * ) Notice: Subject to any disclaimer, the term of this patent is extended or adjusted under 35 U.S.C. 154(b) by 1456 days.

(21) Appl. No.: 11/182,947

(22) Filed: Jul. 18, 2005

(65) Prior Publication Data

US 2006/0018968 A1    Jan. 26, 2006

Related U.S. Application Data

(60) Provisional application No. 60/589,395, filed on Jul. 20, 2004.

(51) Int. Cl.
*C08G 61/02* (2006.01)

(52) U.S. Cl.
USPC .......................................................... 523/1

(58) Field of Classification Search
None
See application file for complete search history.

(56) References Cited

U.S. PATENT DOCUMENTS

| | | | | |
|---|---|---|---|---|
| 4,799,962 A | 1/1989 | Ahmed | ......................... | 106/188 |
| 5,487,777 A | 1/1996 | Lundan et al. | ................. | 106/188 |
| 5,932,193 A | 8/1999 | Lopez et al. | ..................... | 424/52 |
| 6,093,769 A | 7/2000 | Burdick et al. | ................ | 524/767 |

FOREIGN PATENT DOCUMENTS

| | | |
|---|---|---|
| WO | 01/81476 | 11/2001 |
| WO | 02/17869 | 3/2002 |

*Primary Examiner* — Paul Dickinson
(74) *Attorney, Agent, or Firm* — Shaorong Chen; Joanne Rossi; Michael J. Herman

(57) ABSTRACT

An aqueous based functional system contains a stable fluid polymer suspension (FPS) thickening agent of a polysaccharide, polyethylene glycol (PEG), and hydrated thickening silica. The functional systems may be formulations of personal care excluding oral care, household care, oil field servicing fluids, Civil Engineering servicing fluids, paper coatings, construction fluids, ceramic glazes, foods, firefighting retardants, mineral processing, aqueous based coatings, building materials, construction, pharmaceuticals, medical care, paper making process, and paper coating. The FPS provides to the functional system comparable or better rheology and viscosity properties as compared to when using similar thickening agents in dry, solid form. A method of preparing the aqueous based functional system is also provided by adding a sufficient amount of a stable FPS that is compatible with the functional system to the system to thicken the functional system.

70 Claims, No Drawings

USE OF POLYETHYLENE GLYCOL BASED FLUIDIZED POLYMER SUSPENSION IN FUNCTIONAL SYSTEMS

RELATED APPLICATIONS

This application is related to and claims the benefit of U.S. Provisional Patent Application Ser. No. 60/589,395, filed Jul. 20, 2004, the disclosure of which is incorporated herein by reference.

FIELD OF THE INVENTION

This invention relates to functional systems using a stable, easy-to-use, Food and Drug Administration (FDA) food contact approved rheology modifier in the form of a fluidized polymer suspension (FPS). More particularly, this invention relates to functional systems containing FPS of water-soluble polymers and polyethylene glycol (PEG) and derivatives thereof.

BACKGROUND OF INVENTION

Water-soluble polymers (WSPs) are well known in the prior art as rheology modifiers of aqueous functional systems. For instance, they are used as thickeners for a wide range of functional systems such as for latex paints, oil-well servicing fluids, cosmetics, personal care products, construction and building products, Civil Engineering applications, household care products, food, and paper manufacturing products. Civil Engineering applications include diaphragm walling and trenching, pilling, water-well drilling, horizontal drilling and tunneling. It is also well known that these WSPs sometimes have problems of lumping, dispersability, and pourability in dry form. Therefore, dispersions or fluid polymer systems (FPS) are well accepted in many industries.

The most commonly used WSPs as thickeners are guar and guar derivatives, carboxymethylcellulose (CMC), and hydroxyethylcellulose (HEC). All these products have been patented in dispersions or suspensions (or FPS) systems for various uses using organic carriers such as fatty acids, diesel or mineral oils. Current technologies for CMC, HEC and guar/derivatives suspensions are based on the use of either fatty acids and/or mineral oil as the carrier. Both of these technologies have limitations in certain markets.

Polyethylene glycol (PEG) is used widely in many industries, especially the low molecular weight products. Ethylene glycol and its lower polyglycols are colorless, odorless, hygroscopic liquids that have high boiling point and are completely miscible in water and many organic liquids. PEG markedly reduces the freezing point of water. PEG at low level can be administered orally and has been approved by the Food and Drug Administration.

PEG has a variety of uses. In the food industry, it is used as a solvent, humectant, and preservative, in the manufacture of products that come in contact with food such as plasticizers for food wraps, as a solvent for food processing, and as lubricant for food machinery. It is a softening agent, spreader, emollient, intermediate, drug vehicle and preservative in the preparation of cosmetics and pharmaceuticals. Aqueous solutions of PEG are effective antifreeze mixtures and are preferred in refrigeration units in breweries, dairies and packing houses, where a coolant or heat-transfer solution of low toxicity is important. These aqueous solutions prevent rust and corrosion.

U.S. Pat. No. 5,932,193, (J-P Lopez, M. Melbouci, and G. Dewald) discloses an invention involving the use of a PEG based suspension for use in toothpaste formulations. All additives in the slurry composition are used in oral care applications. The preferred composition of the suspension was specified as (a) 40-60% of polyethylene glycol, (b) 0.5-2.0% of amorphous fumed silica, and (c) 40-60% of CMC.

U.S. Pat. No. 5,487,777 (Lunden et al) discloses stable carboxymethyl cellulose (CMC) slurries of 10-60 wt % of CMC, 40-60 wt % of water-soluble polyethylene glycol, and 1-50 wt % of an inert powder or dispersion. This slurry is used as a rheology modifier in aqueous liquid applications such as clarification of water, treatment of minerals, the thickening of foodstuffs and medication, the thickening of farm products, the use of oil drilling liquids, the use of building materials, and the modification of latex colors.

U.S. Pat. No. 4,799,962 (Ahmed) discloses dispersions of water-soluble polymers in low molecular weight polyethylene glycol, water, and high molecular weight polyethylene glycol in amounts sufficient to impart stability to the dispersion. These dispersions are used in latex paints.

U.S. Pat. No. 6,093,769 (Burdick et al.) discloses fluidized polymer suspensions of cationic polysaccharides, stabilizing agent and water-soluble polyols. The preferred cationic polysaccharides are cationic guar and cationic hydroxypropyl guar. Process for preparing personal care compositions utilizing fluidized polymer suspensions in the process provides advantages of more rapid dissolution and avoidance of lumps and gels when compared to powdered cationic polysaccharides.

Since it is well known in the prior art that the use of dry polysaccharides and prior art dispersion techniques are time consuming, inefficient, and not at all time compatible with the functional systems in which they are added, there remains a need in the industry for incorporating water-soluble binder polymers in to functional systems which provide lump-free products, rapid viscosity development, reduced batch preparation time, compatibility, and convenient handling of the binder.

None of the above mentioned prior art meets all of the requirements of the needs of the industries.

SUMMARY OF THE INVENTION

The present invention is directed to a composition of an aqueous based functional system and a stable fluid polymer suspension (FPS) thickening agent of a polysaccharide, polyethylene glycol (PEG), and hydrated thickening silica. The FPS provides to the composition comparable or better rheology and viscosity properties as compared to when using similar thickening agents in dry, solid form.

The aqueous based functional system of the present invention can be any water soluble system that uses water based rheology modifiers. For example, the functional systems may be formulations of personal care excluding oral care, household care, oil field servicing fluids, Civil Engineering servicing fluids, paper coatings, construction fluids, ceramic glazes, foods, firefighting retardants, mineral processing, and aqueous based coatings such as latex paints, building materials and construction, pharmaceutical, medical care, paper making process and paper coating.

The present invention is also related to a method of preparing an aqueous based functional system comprising adding a sufficient amount of a stable fluid polymer suspension (FPS) that is compatible with the functional system to the aqueous based functional system to thicken the functional system. The FPS includes a polysaccharide, polyethylene glycol, and hydrated thickening silica.

DETAILED DESCRIPTION OF THE INVENTION

It was surprisingly found that the present invention expands the scope of applications for PEG based suspensions beyond the uses disclosed in the prior art. It has been found that aqueous based functional systems, when using an FPS of a polysaccharide, PEG, and hydrated thickening silica, will provide a product that has comparable or better rheology and viscosity properties as compared to when using similar prior art thickening agents. The FPS not only eliminates the problems of lumping and slow dispersion as compared to when using dry polymer, but also provides a more hazard free environment, more efficient system, a more tailored system for a particular task, and, in certain instances, multiple tasks in the system.

In accordance with the present invention, the fluidized polymer suspension is basically a suspension of a polysaccharide in polyethylene glycol. In the suspensions, the polysaccharide is in the form of a finely divided solid. Preferably, the particle size distribution of the polysaccharide is such that about 80% of the particles have a size less than about 75 μm.

The PEG based materials used in this invention are environmentally friendly and exhibit the desirable traits of suspension stability, low toxicity, and low volatile organic compound (VOC) content. The PEG based fluid polymer suspensions may be used where addition of fatty acid or mineral oil suspensions are problematic and may provide additional functionality, such as pigment dispersion in paper coatings and anti-freezing agent in paints.

Although any water miscible, liquid polyethylene glycol may be used in the fluidized polymer suspension of the present invention, the preferred PEGs are those with mean average molecular weight (Mw) of less than about 1,000. More preferred are the PEGs with Mw of less than about 700, and most preferred are those with Mw of about 200 to about 400.

The ingredients, contained in the composition of the PEG based FPS of the present invention, are approved by the FDA for use in food contact. PEG 300 and 400 are approved under 21 CFR 176.170 and 176.180 (PEG 200 not listed) and Aerosil 200 silica (a component of defoaming agents used in the manufacture of paper and paperboard), complies with FDA regulation under 21 CFR 176.200 and 176.210 for use as indirect food additive. Furthermore, both PEG 300/400 and Aerosil silica are used in oral care applications in contact with mucous membranes.

The chemical structure of polyglycols gives them very low friction factors, high viscosity indices and minimal pressure-viscosity dependence. They also show little sensitivity to shear stress. These properties make them interesting candidates for lubricant applications. The melting point of PEGs is about −50° C. for a molar mass of about 200 g/mol, −15° C. for a molar mass of 300 g/mol, and above 0° C. for a molar mass of 400 g/mol and higher, so that these substances are suitable for many lubrication uses.

In accordance with the present invention, normally, the maximum amount of the PEG used in the fluidized polymer suspension is about 90% by weight based on the total weight of the FPS. Preferably, the maximum (or upper limit) amount of the PEG is 80 wt % and more preferably 70 wt %. The normal minimum (or lower limit) amount of the PEG is about 40 wt %, preferably 50 wt %, and more preferably 60 wt %.

Hydrated thickening silica is incorporated in the FPS of the present invention to serve as a suspending agent for the dispersed water-soluble polymer. Hydrated thickening silicas are synthetic silicas including fumed silicas, amorphous precipitated silicas, and gel silicas. Fumed silica forms a random network that is impossible to observe the crystalline components by IR (Degussa Technical Bulletin #11). The fumed silica has a small particle size (approx. 10 μm) and large surface area (200 to 300 sq. m/g). This makes them very effective for thickening, thixotropy, and as a suspending vehicle at low concentrations.

The upper limit (or maximum) amount of hydrated thickening silica that is used in the FPS of the present invention is about 3.0% by weight based the total weight of the FPS, preferably 2.0 wt %. The lower limit amount of the hydrated thickening silica is about 0.1 wt %, preferably 0.5 wt %.

In accordance with the present invention, the polysaccharides include cellulosic derivatives, guar gum, guar derivatives, starch and starch derivatives, polyvinyl alcohol (PVA), polyacrylates/polyacrylamides (PAAC/PAAM) and biopolymers such as wellan gum and xanthan gum. The cellulose derivatives include hydroxyethylcellulose (HEC), carboxymethyl cellulose (CMC), carboxymethyl hydroxyethyl cellulose (CMHEC), polyanionic cellulose (PAC), methyl cellulose (MC), and MC derivatives. The HEC, however, did not produce the desired long-term stability of the suspension as other polysaccharides. Because of HEC's swellability in the PEG, the resulting suspensions had a tendency to build-up viscosity over time. Examples of the biopolymers include wellan gum and xanthan gum. Examples of the guar derivatives include hydroxyethyl guar (HEG), hydroxypropyl guar (HPG), carboxymethyl hydroxypropyl guar (CMHPG) and carboxymethyl guar (CMG). Examples of methyl cellulose derivatives are hydroxypropyl methyl cellulose (HPMC), hydroxyethyl methyl cellulose (HEMC), and carboxymethyl methyl cellulose (CMMC).

The upper limit (or maximum) amount of the polysaccharide that is used in the FPS of the present invention is about 60.0% by weight based the total weight of the FPS, preferably 50.0 wt %, and more preferably 40.0 wt %. The lower limit amount of the polysaccharide is about 10.0 wt %, preferably 20.0 wt %, and more preferably 30.0 wt %.

In accordance with the present invention, the unique rheology of the PEG based FPS provides high thickening efficiency, and stabilizes emulsions and suspensions. The polysaccharides of the present invention provide significantly enhanced performance over known prior art systems in aqueous functional systems including personal care formulations (i.e., skin care, hair care, and sunscreen care), medical care (i.e., wound care and ostomy), food applications (i.e., tortillas, cake mixes, bread mixes, bread, ice cream, sour cream, pasteurized processed cheese spreads, and cheese foods), beverages (i.e., instant cold/hot drinks, ready to drink beverages, and fruit flavored drinks), food packaging, aqueous based coatings (i.e., latex paints), building and construction materials (i.e., joint formulations and ceramic glazes), mineral processing, oil field formulations (e.g., drilling fluids, completion fluids, and fracturing fluids), Civil Engineering, paper making and paper coating formulations, and pharmaceutical formulations.

In accordance with the present invention, the functional system can either be prepared in a continuous or batch process and either in a stepwise addition of the ingredients or a simple dumping of all of the ingredients at once. The order of addition of the ingredients can also vary over a wide range of additions. For example, the functional ingredients can be individually added one at a time to the FPS or all at once or the FPS can be added directly to the formulated ingredients in a single step. Hence, the process of thickening an aqueous based functional system (i.e., personal care products excluding oral care, household care products, oil field servicing fluids, civil engineering servicing fluids, paper coating products, construction fluids, ceramic glazes, foods, firefighting retardants, mineral processing products, and water based protective coatings), includes adding and mixing a sufficient amount of a stable fluid polymer suspension that is compatible with the aqueous based functional system to thicken the functional system, wherein the stable fluid polymer suspension comprises a polysaccharide, polyethylene glycol, and hydrated thickening silica. The resulting functional system has comparable or better rheology and viscosity properties as compared to when using similar thickening agents in dry, solid form. This process is also more efficient and more versatile so that it can be prepared in the field or at work site where it can be customized to suit the environment in which it is to operate. This process is extremely user friendly.

Personal Care

At present, most of the polymeric additives for the personal care and cosmetics industry are primarily supplied in dry powder form. Use of dry powders can present problems related to dust generation. They may also be difficult to disperse to form lump-free solutions. It is believed that these problems will be eliminated through the use of a fluidized polymer suspension. As with the other applications mentioned above, the use of PEG as the suspending vehicle should prove more acceptable to the industry than currently available suspension technologies.

PEGs are used as additives and adjuvants in many different pharmaceutical and cosmetic applications on the basis of their physiological harmlessness. Many PEG types have received INCI designations as cosmetic components. The application profile reaches from maintaining moisture levels in creams and toothpaste to binding agents in tablets, water-soluble tablet coatings and used as adjuvants in laxative formulae.

Being totally miscible in water, PEG based FPS systems are particularly useful in hair and skin compositions, especially in clear formulations, without depositing an undesired substance that could result from use of an incompatible FPS carrier. When dissolved in water, the PEG FPSs exhibit crystal clear solution, well comparable to the powdered precursor, with the advantage of easy handling and quick dissolving to produce clear and lump-free solutions.

When used in personal care compositions such as, but not limited to, facial scrub formulae, emulsifier-free emulsions or clear conditioners, it is anticipated that PEG/CMC based FPS compositions (FPS 1-1 to 1-3 and FPS 5-1 of Tables 1-a and 5-a, below) would provide homogeneous and stable emulsions. Furthermore, when used in combination with synthetic Hectorite clay, the PEG/CMC suspensions would provide a good suspending capacity of PE abrasive beads in facial scrub compositions.

In accordance with the present invention, when the composition is a personal care composition, it includes (a) from about 0.1% to about 99.0% by weight of the vehicle component and (b) at least one active personal care ingredient.

In accordance with the present invention, the personal care active ingredient must provide some benefit to the user's body. Personal care products include haircare, skincare, and suncare products. Examples of substances that may suitably be included in the personal care products according to the present invention are as follows:

1) Perfumes, which give rise to an olfactory response in the form of a fragrance and deodorant perfumes which in addition to providing a fragrance response can also reduce body malodor;
2) Skin coolants, such as menthol, methyl acetate, methylpyrrolidone carboxylate N-ethyl-p-menthane-3-carboxamide and other derivatives of menthol, which give rise to a tactile response in the form of a cooling sensation on the skin;
3) Emollients, such as isopropylmyristate, silicone oils, mineral oils and vegetable oils which give rise to a tactile response in the form of an increase in skin lubricity;
4) Deodorants other than perfumes, whose function is to reduce the level of or eliminate micro flora at the skin surface, especially those responsible for the development of body malodor. Precursors of deodorants other than perfume can also be used;
5) Antiperspirant actives, whose function is to reduce or eliminate the appearance of perspiration at the skin surface;
6) Moisturizing agents, that keeps the skin moist by either adding moisture or preventing moisture from evaporating from the skin;
7) Cleansing agents, that removes dirt and oil from the skin;
8) Sunscreen active ingredients that protect the skin and hair from UV and other harmful light rays from the sun. In accordance with this invention a therapeutically effective amount will normally be from 0.01 to 10% by weight, preferable 0.1 to 5% by weight of the composition;
9) Hair treatment agents, that conditions the hair, cleans the hair, detangles hair, acts as styling agent, volumizing and gloss agents, anti-dandruff agent, hair growth promoters, hair dyes and pigments, hair perfumes, hair relaxer, hair bleaching agent, hair moisturizer, hair oil treatment agent, and anti-frizzing agent;
10) Shaving products, such as creams, gels and lotions and razor blade lubricating strips;
11) Tissue paper products, such as moisturizing or cleansing tissues;
12) Beauty aids, such as foundation powders, lipsticks, and eye care; and
13) Textile products, such as moisturizing or cleansing wipes.

Household Care

In accordance with the present invention, when the composition is a household care composition, it includes (a) from about 0.1% to about 99.0% by weight of the vehicle component and (b) at least one active household care ingredient.

In accordance with the present invention, the household care active ingredient must provide some benefit to the user. Examples of substances that may suitably be included according to the present invention are as follows:

1) Perfumes, which give rise to an olfactory response in the form of a fragrance and deodorant perfumes which in addition to providing a fragrance response can also reduce odor;
2) Insect repellent agent whose function is to keep insects from a particular area or attacking skin;
3) Bubble generating agent, such as surfactants which generates foam or lather;
4) Pet deodorizer such as pyrethrins which reduces pet odor;
5) Pet shampoo agents and actives, whose function is to remove dirt, foreign material and germs from the skin and hair surfaces;
6) Industrial grade bar, shower gel, and liquid soap actives that remove germs, dirt, grease and oil from skin, sanitizes skin, and conditions the skin;
7) All purpose cleaning agents that remove dirt, oil, grease, and germs from the surfaces in areas such as kitchens, bathroom, and public facilities;

8) Disinfecting ingredients that kill or prevent growth of germs in a house or public facility;
9) Rug and Upholstery cleaning actives which lift and remove dirt and foreign particles from the surfaces and also deliver softening and perfumes;
10) Laundry softener actives which reduce static and makes fabric feel softer;
11) Laundry detergent ingredients which remove dirt, oil, grease, and stains and kill germs;
12) Dishwashing detergents which remove stains, food, germs;
13) Toilet bowl cleaning agents which remove stains, kill germs, and deodorize;
14) Laundry prespotter actives which help in removing stains from clothes;
15) Fabric sizing agents which enhance appearance of the fabric;
16) Vehicle cleaning actives which remove dirt, grease, etc. from vehicles and equipment;
17) Lubricating agents which reduce friction between parts; and
18) Textile products, such as dusting or disinfecting wipes.

The above list of personal care and household active ingredients are only examples and are not a complete list of active ingredients that can be used. Other ingredients that are used in these types of products are well known in the industry. In addition to the above ingredients conventionally used, the composition according to the present invention can optionally also include ingredients such as colorants, preservatives, antioxidants, nutritional supplements, activity enhancers, emulsifiers, viscosifying agents (such as salts, i.e., NaCl, $NH_4Cl$ & KCl), water-soluble polymers (e.g., hydroxyethylcellulose), and fatty alcohols (e.g., cetyl alcohol), alcohols having 1-6 carbons, and fats and oils.

The rheology modifiers of the present invention may also be used in combination with other known rheology modifiers including, but not limited to, polysaccharides (e.g., carrageenan, hyaluronic acid, glucosaminoglycan), biopolymers (e.g., xanthan gum), synthetic polymers, and abrasive/thickening silicas.

Protective Coatings

Water-based protective coating compositions (commonly referred to as paints) in which cellulose ether derivatives are conventionally used include latex paints or dispersion paints, of which the principal ingredients are film-forming latices such as styrenebutadiene copolymers, vinyl acetate polymers and copolymers, and acrylic polymers and copolymers. Typically, they also contain opacifying pigments, dispersing agents and water-soluble protective colloids, the proportions being, by weight of the total composition, about 10 parts to about 50 parts of a latex, about 10 parts to about 50 parts of an opacifying pigment, about 0.1 part to about 2 parts of a dispersing agent, and about 0.1 part to about 2 parts of a water-soluble protective colloid.

Water-soluble protective colloids conventionally used in the manufacture of latex paints (to stabilize the lattices and maintain the wet edge of a painted area longer in use) include casein, methyl cellulose, hydroxyethylcellulose (HEC), sodium carboxymethyl cellulose (CMC), polyvinyl alcohol, starch, and sodium polyacrylate. The disadvantages of the natural based cellulose ethers is that they may be susceptible to biological degradation and frequently impart poor flow and leveling properties, while the synthetic materials such as polyvinyl alcohol often lack enough thickening efficiency to maintain sag resistance. The thickening efficiency of the cellulose ethers are usually improved by increasing their molecular weight which normally is more expensive.

Polyglycols are completely miscible in water and are used as non-volatile solvents and substrates for paints, inks and adhesives. Due to polyglycols reduced tendency to evaporate, they prevent the mixtures from drying out and help disperse pigments. Polyglycols are currently used in architectural paints for maintaining flow and leveling of paint after most of the aqueous phase has evaporated. They further act as an anti-freeze in water-borne paint, which is helpful in retaining freeze-thaw resistance. They can also be used as foam regulators and defoaming agent in coatings and paints. Therefore, there is clear benefits in using PEG based CMC suspension of the present invention combining the thickening and water binding efficiency of CMC with the above advantages brought by the PEG which serves as a carrier for the suspension.

Paper Coatings

Paper coating is a process in which the surface structure of paper or board is improved by the application of a mineral coating which subsequently is dried. Coating process is the application of a water-based pigment slurry, which is bound at the surface by one of several binders. Other coating components are added to obtain a suitable rheology, and to impart properties such as brightness or water resistance.

Coated paper, such as that used in magazine and catalogue sectors, is printed, although some special grades are produced for other purposes. The primary purpose of coating is to achieve optimum printing quality by improving the surface properties of the base paper, such as smoothness, brightness, gloss, printing gloss. This is a result of the coating layer that has a considerably more even and finer pore structure than the base paper. The smoothness on the paper is improved, since the relatively big holes on its surface are filled by coating. A secondary purpose is the improvement of optical properties of the paper. Better appearance in obtained by improving gloss, opacity and brightness. Coating can give the paper either a very high gloss or a low one. The degree of gloss desired depends, of course, on the use of paper. This means that the requirements on coated papers are both mechanical and optical.

A coating process can generally be divided into three different phases: (1) Preparation of the coating formulation (known as called coating color), (2) Coating and (3) drying. The general principles of formulating paper coating are mostly well known. Moreover, each paper maker has his own tailor-made recipes for his specific requirements. Therefore, it would not be feasible to give a "recipe" for a specific coating process, coating type or printing process. However, a generic coating formulation recipe contains 75-90% pigment (such as clay, satin white, calcium carbonate, titanium dioxide, talc, aluminum hydroxide, calcium sulfate, barium sulfate, synthetics, etc.), 0.10-0.50% dispersant, 0.05-0.30% alkali, 5-20% binders (such as styrene butadiene lattices, acrylics, polyvinyl acetate, starch and starch derivatives, proteins (casein, soya) and 0-2% co-binder (cellulose ethers, polyvinyl alcohol and solution or emulsion polyacrylate). Other functional additives such as lubricants, OBA and defoamers are often added into the coating formulation. All amounts of ingredients are based on weight of pigment.

Even though the coating formulation contains only a small amount of PEG based CMC FPS, it influences the properties of the paper. In accordance with the present invention, PEG based FPS provides numerous functional benefits, such as:
Pigment dispersion
Water retention
Binding power
Rheology control
Stabilization of the coating color Optical brightening effect
Gloss
Wet rub resistance
Increased blade life, more particularly through the lubrication action PEG is promoted as a low volatility additive for paper coatings. It is reported that "PEGs disperse pigments and act as a plasticizer". Based on slurry stability information available in prior art, the PEG based suspensions of the present invention were found to provide adequate handling properties with reasonably low overall viscosity.

In addition to paper coating, PEG based CMC FPS of the present invention can be used in papermaking process and for surface sizing. In papermaking process, the PEG based CMC FPS is used as an additive in the stock as a refining agent, wet-strength agent, dry strength agent, internal bonding agent, water retention agent and improving the sheet formation. For surface sizing, the PEG based CMC FPS is used as binding agent and aids in film formation, reduces the porosity and hold out, and boosts the optical brightener.

Oilfield Servicing Fluids

Drilling an oil or gas well is a complex operation, involving several steps prior and after the well is put into production. Primary oil-recovery operations include drilling the well, cementing the casing to the formation and completing the well prior to oil or gas production. Workover operations may be necessary during remedial work in producing wells, usually as an attempt to enhance or prolong the economic life of the well. When the flow rate of the fluid is diminished, the reservoir may be treated in some manner to increase the flow of fluid into the wellbore. This operation is called secondary recovery, known as fracturing/stimulation operations. They are performed either by acid wash or hydraulic fracturing. When the reservoir is depleted, enhanced oil recovery operations may be needed to increase the production rate. This operation is called tertiary recovery, and involves injection of fluids into the formation surrounding the production well to increase the flow rate of the formation fluid into the wellbore.

Drilling fluids are an integral element of the drilling program for primary oil recovery. They are especially designed to perform numerous functions that condition the success of drilling operations. Their principal functions include, but not limited to, are:
An effective hole cleaning efficiency (H.C.E.).
Maintaining the stability of the open hole-formation.
Formation of a thin and low-permeability filter cake on the formation.
Minimizing formation damage.
Friction reduction between the drilling string and the formation.
Cool and clean the bit.

To perform these functions, drilling fluids should possess particular properties with regard to rheology, density, and filtration control. Filtration control is a key performance attribute that affects all other properties. In fact, loss of significant amount of water from the drilling fluid into the formation would result in irreversible change of the overall drilling fluid properties (density and rheology) that would seriously affect the stability of the borehole.

Drilling fluids can be classified on the basis of their principal constituent (continuous phase). The continuous phase may be water, oil, or gas. The resulting drilling fluids are called water-based mud, oil-based mud, or foam mud, respectively. The rheology modifiers of the present invention are particularly suitable for water-based muds and foam muds.

Among a variety of additives, carboxymethyl cellulose (CMC) and polyanionic cellulose (PAC) are widely used as a commodity material to optimize water-based drilling fluid properties. High-viscosity types are used for rheology and fluid loss control properties while low viscosity types are exclusively used for filtration control properties. In most cases, both types are used together in a drilling fluid composition. During drilling operations, optimum drilling fluid attributes are further achieved by combining different components including clay, CMC/PAC, xanthan gum (primary rheology modifier), starches (improved filtration control) and other synthetics polymers that may be required for dispersing or shale inhibition properties.

Completion and workover fluids are specialized fluids used during well completion operations and remedial workover procedures. They are placed across the chosen payzone after the well has been drilled but prior to putting it on production. These fluids must control not only subsurface pressure with density, but also must minimize formation damage during completion and workover operations to improve oil or gas production rate. Because all wells are susceptible to formation damage to some degree (from a slight reduction in the production rate to complete plugging of specific zones) and the potential for permanent damage is greater during completion and workover operations than it is during drilling, it is imperative to use a fluid that causes the least possible damage to the pay zone formation. The principal functions of completion and workover fluids include, but not limited to, are:
Control subsurface pressures.
Minimize formation damage.
Maintain well bore stability.
Control fluid losses to the formation.
Transport solids.
Maintain stable fluid properties.

The types of completion and workover fluids can be categorized into clear solids-free brines, polymer viscosified brines with bridging/weighting agents, and other fluids including oil base, water base, converted muds, foam, etc. The primary selection criteria for an appropriate completion or workover fluid are density. Clear, solids free brines are the most commonly used fluids and are viscosified with polymers (CMC/PAC, xanthan gum, guar and guar derivatives, and HEC) and may incorporate solids that can be dissolved later, such as acid soluble calcium carbonate or sized sodium chloride salt, for increased density or bridging purposes. While HEC is the most suitable polymer for brine based systems, CMC/PAC and xanthan gum find their use in low density (up to 12 ppg) monovalent salts based brines.

Hydraulic fracturing may be defined as the process in which fluid pressure is applied to the exposed reservoir rock until failure or fracturing occurs. After failure of the rock, a sustained application of fluid pressure extends the fracture outward from the point of failure. This may connect existing natural fractures as well as provide additional drainage area from the reservoir. The fluid used to transmit the hydraulic pressure to the reservoir rock is called the fracturing fluid. To prevent the fracture from closing when pumping is stopped, propping agents, such as sized sand, are added to the fracturing fluid. The propping agent acts as supports to hold the fracture open after the treatment and to provide an improved ability of the fracture to conduct oil or gas through the fracture to the wellbore. The polymers of choice in hydraulic fracturing operations are guar and guar derivatives.

For easy handling in oil and gas well rigs, oilfield operations, especially offshore, require the use of liquid substances/preparations whose discharge from offshore installations does not need to be strongly regulated. The substances should not be harmful to the environment.

Due to variable climate conditions to which the substances/preparations are subjected during their use and storage (i.e., high summer temperatures in the Gulf of Mexico (GOM) and extremely low winter temperatures in the North Sea territory). There is a desire in the oilfield market for polymer suspensions that are stable, environmentally friendly, and meet all discharge regulations. There are presently suspensions of WSPs available either in white medicinal oil, such as AquaPAC® Liquid, Natrosol® Liquid or Galactasol® Liquid (all available from Aqualon), or in glycols, such as Xanthan/glycol methyl ether, HEC/Butyl di-glycol and Guar/polyglycols. While the white mineral oil FPS meets most of the requirements, such as long-term stability, low viscosity, and high active content (i.e. $\geq$40 wt. %), they do have some regulatory use limitation. Despite this, they still meet the requirements for use in the North Sea, but they do not pass the EPA 1664 oil and grease test (extraction with hexane) for use in the GOM. Comparatively, while the commercially available glycol suspensions meet the environmental requirements for use in GOM, they have tendency to thicken over time, hence causing problems of handling after storage.

Civil Engineering Servicing Fluids

Civil engineering applications include tunneling, diaphragm walling, pilling, trenching, horizontal drilling, and water-well drilling. These applications are often characterized by their closeness to agglomerations where strict environmental regulation is in effect to minimize any kind of pollution or contamination. The corresponding working sites are further characterized by the availability of very poor mixing equipment on-site to efficiently disperse and dissolve the WSPs. There is a desire in civil engineering applications for polymer suspensions that are stable, environmentally friendly, and meet all discharge regulations.

Construction/Building Compositions

Building compositions, also known as construction materials, include concrete, tile cement and adhesives, projection plasters, stuccos based on cement and synthetic binders, ready mixed mortars, manually applied mortars, underwater concrete, joint cement, joint compounds, gypsum board, crack fillers, floor screeds, and adhesive mortars. These compositions are essentially Portland cements, Plaster of Paris or vinyl copolymers containing functional additives to impart characteristics required for various construction applications. While lime was once the preferred material for controlling the water ratio in the building compositions, cellulose ethers are at present time the most used because of their contribution to improve the water retention characteristics and other physical properties such as workability, consistency, open time, tack, bleeding, adhesion, set time, and air entrainment.

PEG based cellulose ether FPS as well as PEG based guar and derivatives FPS of the present invention have use applications in the above building compositions.

Ceramic Bodies/Glazes

The current industry standard is dry CMC powders. These are typically added to ceramic body and glaze formulas prior to the milling process. The milling process, shearing, heating, and mixing of the glaze paste promote the hydration of the polymer. It is believed that the increased viscosity provided by the polymer slows the milling process and the use of dry polymer also limits the ability to adjust the viscosity of the glaze after milling. By adding a fluidized CMC suspension to the glaze formulation after the milling process, the throughput and accuracy of the final glaze viscosity are improved. Furthermore, fluidized CMC suspensions offer the possibility of post-adjustment of the viscosity when required. In most cases, for easy handling and processing, low to medium Mw CMCs are most preferred for use in ceramics. For quality consistency from batch to batch, the fluidized CMC suspensions should possess a reasonably low viscosity combined with excellent stability.

Foods

PEGs are currently approved for a variety of direct food additive uses as described in Title 21 of the Code of Federal Regulations (CFR). As with the personal care applications mentioned above, use of water-soluble polymers suspended in PEG provide improved ease of use. Improved plant sanitation also result (due to dust free nature of the product).

PEG/CMC FPS of the present invention may be used in food and food packaging as a two-in-one component. Being odorless and tasteless, PEG carrier of the present invention would provide additional attributes over the primarily additive (CMC) such as enhanced moisture retention, improved texture, body and mouthfeel in baked goods, syrups and pet-food. It would further impart lubrication properties in animal feeds (extrusion products).

Miscellaneous

Firefighting:

Customers in the industry requested liquid products with the thought that they could move polymer to the field and mix on the fly. The interest behind it is that highly loaded fluidized polymer suspensions could be metered into the aircraft tanks along with water at different rates to "dial in" the viscosity depending on the weather/height of drop/ground cover etc. This is better for them rather than mixing a bulk tank of retardant and having to use that viscosity regardless of other factors contributing to the general drop conditions. Ease of handling and rapid hydration are key performance parameters for improved field usage/handling. Also "environmentally friendly" components are important. PEG/CMC FPS as well as PEG/Guar and derivatives FPS meet all these requirements. Typically the Guar and derivatives used in this application are HP guar and CM guar.

Mining/Metal Processing:

Despite poorer electrowinning performance, liquid polyacrylamides (often solutions) are gaining market interest due to their ease of handling and safer product to work with due to no dusting/producing slick areas. CMC and Guar can be used in a number of applications in mining, but the two predominant uses would be as talc depressants or electrowinning process aids. Unlike liquid polyacrylamide, in addition to their easy handling and rapid hydration, PEG/CMC FPS as well as PEG/Guar and derivatives FPS would provide key performance advantages with improved electrowinning properties over liquid polyacrylamides. Either Guar gum or Guar derivatives (HP Guar and CM guar) may be used in mining.

The following Examples are merely set forth for illustrative purposes, but it is to be understood that other modifications of the present invention within the skill of an artisan in the related industry can be made without departing from the spirit and scope of the invention. All percentages and parts are by weight unless specifically stated otherwise.

Example 1

The following PEG FPS compositions of MHPC. HM-HEC and Cat. Guar as an additive in personal care illustrates the unexpected suspensions flexibility of the present invention.

TABLE 1-a

Polymer Suspensions for Personal care

| Additive | Trademark | FPS 1-1 | FPS 1-2 | FPS 1-3 |
|---|---|---|---|---|
| Polyethylene glycol | PEG 400 | 74% | 58.5% | — |
|  | PEG 200 | — | — | 65% |
| Thickening silica | Aerosil 200 | 0.95% | 1.5% | 1.67% |
| MHPC |  | — | 25% | — |
| Cationic Guar | N-Hance 3000 | — | 40% | — |
| HM-HEC | Natrosol Plus 331 | — | — | 33.33% |
| Brookfield Viscosity, cPs | After Preparation | 2820 | 2090 | 2650 |
|  | After 24 hrs aging | — | — | gel |

Application in Hand and Body Lotion

A hand and body lotion composition was prepared with Natrsosol Plus 331, available from Aqualon (Table 1-b). The PEG suspension (FPS 1-3) of the present invention was compared to its dry precursor at 0.5% active basis. Part of the glycerin and mineral oil in the composition 1 was replaced by the PEG brought by the suspension FPS 1-3 in the composition 2.

It can be seen from the Table 1-b that the PEG based suspension of Natrosol Plus 331, subject of this invention, is an effective thickener of hand and body lotion compositions, providing about 6% higher final viscosity than the dry precursor.

TABLE 1-b

Hand and body Lotion composition

| Part | Ingredient | Composition 1 | Composition 2 |
|---|---|---|---|
| A. | Natrosol Plus 331, dry | 0.50% | — |
|  | PEG/Natrosol Plus 331, FPS (FPS 1-3) | — | 1.51% |
|  | Distilled water | 78.73% | 78.65% |
|  | Glycerin USP | 2.01% | 2.11% |
| B. | Glycol stearate | 2.77% | 2.77% |
|  | Stearic acid | 2.52% | 2.51% |
|  | Mineral Oil | 2.01% | 1.00% |
|  | Acetylated lanolin | 0.50% | 0.50% |
|  | Cetyl alcohol | 0.25% | 0.25% |
| C. | Distilled water | 10.06% | 10.05% |
|  | Triethanolamine | 0.50 | 0.50 |
| D. | Biocide | 0.14% | 0.14% |
|  | Brookfield Helipath model DV-I, |  |  |
|  | Viscosity, Spindle T-F, 1.5 rpm | 462,067 cPs | 492,833 cPs |

Preparation Procedure

Both preparations were made on the same active polymer basis (0.50 wt. %). To compensate for the additional PEG400 humectant fluid present in the FPS recipe, the content of the mineral oil was reduced from the control formulation with the same amount of PEG400 brought in by the FPS.

1. Disperse Natrosol Plus by adding to the vortex of well-agitated water from Part A. Add glycerin with continued mixing and heat to 80° C. mix for 15 minutes at 80° C.
2. In a separate vessel, blend part B ingredients. Heat to 80° C. and mix well
3. Add Part A and Part B using good agitation. Maintain emulsion temperature at 80° C. with constant stirring.
4. Combine Part C ingredients. Add to emulsion. Mix continuously while cooling to 40° C.
5. add Part D (preservative) to emulsion. Mix well
6. Cool and fill.

Application in Hair Care

A Baby shampoo composition (Table 1-c) was prepared with Cat. Guar (N-Hance 3000, available from Aqualon).

TABLE 1-c

Baby Shampoo composition

| Ingredients | Content |
|---|---|
| D.I. water | 64.75% |
| Makadet BX-131 | 33.25% |
| N-Hance 3000 (FPS 1-2) | 1.5% (0.6% active) |
| Germaben II Preservative | 0.5% |
| LVT Brookfield Viscosity (#2/30 rpm) | 631 cPs |

The preparation was made on the basis of 0.6 wt. % active polymer. Makadet was first added into D.I. water and mixed for 30 minutes. The pH was measured at 6.5. Then, the Cat. guar (FPS 1-2) was added, and the composition mixed for 2 hours. After addition of the preservative, the mixture was mixed for an additional 30 minutes. The pH of the final composition (6.68) was adjusted down to 6.48 with 10% citric acid.

Data in Table 1-c shows that the PEG based suspension of N-Hance 3000, is an effective thickener of shampoo compositions, providing appreciable thickening efficiency at relatively low dosage. Higher viscosity can easily be achieved by increasing the polymer dosage.

Example 2

The following Example further illustrates the usefulness and applicability of PEG based CMC FPS in a typical liquid detergent composition. A fine fabric wash composition (Table 2-a, available from Croda Inc., Parsippany, N.J.) was used in this particular example to demonstrate the thickening efficiency of a PEG based 9H4XF CMC FPS in household care applications.

TABLE 2-a

Unthickened fine fabric wash composition

| Ingredients | Content, wt. % |
|---|---|
| D.I. water | 81.00 |
| Sodium Laureth (3) sulfate | 12.00 |
| Trideceth-7 carboxylic acid (90% activity) | 3.00 |
| NaCl | 4.00 |
| Triethanolamine | q.s. to pH 7–8 |
| Dye, Frangrance, Preservative | q.s. |

The initial Brookfield viscosity of the unthickened fine fabric wash was 69.1 cPs (#1/30 rpm). The thickener was used at 1.2% active content.

Data in Table 2-b shows that the PEG based suspension of 9H4XF CMC, subject of this invention, is an effective thickener of laundry detergent compositions, providing an equivalent viscosity to its dry precursor.

TABLE 2-b

Thickened fine fabric wash

| Ingredients | Content, wt. % | |
|---|---|---|
| Unthickened Fine Fabric wash (Table . . . ) | 98.8% | 97% |
| 9H4XF CMC, #93045 | 1.2% | — |
| PEG based 9H4XF CMC (EPS 5-1) | — | 3% |
| LVT Brookfield Viscosity (#3/30 rpm) | 882 cPs | 915 cPs |

Example 3

The following Example further illustrates the usefulness and applicability of PEG based CMC FPS in a typical Paint application.

Samples of PEG based CMC FPS (FPS 5-1) and its dry precursor (9H4XF) were evaluated in a Ucar 367-60 PVC Vinyl-Acrylic flat paint (Table 3-a). The paints were thickened to a constant thickening efficiency of 5.2 lb/100 gal. (Table 3-b) using a high shear mixer (Dispermat).

TABLE 3-a

Ucar 367-60 PVC Vinyl-Acrylic Flat Paint - Unthickened base paint

| Unthickened Base Paint | Grams/13,000 g |
|---|---|
| Pigment Grind | |
| Water | 1,696.24 |
| Tamale 731 Dispersant | 62.42 |

TABLE 3-a-continued

Ucar 367-60 PVC Vinyl-Acrylic Flat Paint - Unthickened base paint

| Unthickened Base Paint | Grams/13,000 g |
|---|---|
| KTPP | 13.57 |
| Igepal CO-660 Surfactant | 29.85 |
| AMP-95 | 13.57 |
| Propylene Glycol | 234.76 |
| Colloid 640 Antifoam | 25.78 |
| Water | 1,260.65 |
| TiPure R-931 Titanium Dioxide | 2,035.49 |
| Satintone W Calcined Clay | 1,696.24 |
| ECC #10 White Calcium Carbonate | 2,713.99 |
| Then, disperse to Hegman 4 to 5 | |
| Letdown | |
| Ucar Latex 367 | 3,070.88 |
| Texanol Coalescent | 107.20 |
| Colloid 640 Antifoam | 25.78 |
| Proxel GXL Preservative* | 13.57 |
| Total | 12,999.99 |

TABLE 3-b

Ucar 367-60 PVC Vinyl-Acrylic Flat Paint - Thickened Paint

| Thickened Paint | Content |
|---|---|
| Composition | |
| Unthickened Base Paint | 230 g |
| Thickener + Water | 50 g |
| Total | 280 g |
| PH, Initial | 8.5 |
| Solids | |
| Weight | 52% |
| Volume | 33% |
| PVC | 60 |
| Lb/Gal | 11.63 |

At the end of the preparation the resulting thickened paints were evaluated according to standard characterization procedures used in the paint industry.

Data in Table 3-c indicates that the PEG based 9H4XF FPS is a slightly more efficient than its dry precursor, giving a slightly higher Stormer viscosity. Both samples had similar ICI viscosities, leveling and hiding properties. The PEG based CMC FPS however provides a slight improvement on sag resistance than the dry CMC. The dry CMC has a 13% improvement on scrub resistance against the FPS sample.

TABLE 3-c

Comparative evaluation in Ucar 367-6OPVC "thickened" flat paint

| Paint Designation XA-1172-169 | Thickener Description/ Designation | Thickening Efficiency Wt. % | Thickening Efficiency lb/100 gal | Stormer KU Init. | Stormer KU ON | ICI Viscosity, Polses | Levelling | Sag Resistance | Hiding Contr. Ratio | Scrub Resist Cycles |
|---|---|---|---|---|---|---|---|---|---|---|
| 1 | 9H4XF CMC, #93045 | 0.4464 | 5.2 | 96 | 100 | 0.68 | 5 | 12 | 0.9766 | 158, 168 |
| 2 | PEG based 9H4XF CMC (FPS 5-1) | 0.4457 | 5.19 | 99 | 104 | 0.72 | 5 | 14 | 0.9770 | 135, 147 |

Example 4

The following CMC based FPS compositions as an additive to a paper coating illustrates the unexpected results of the present invention.

TABLE 4-a

CMC Suspensions for Paper Coatings

| Additive | Trade name | FPS 4-1 | FPS 4-2 |
|---|---|---|---|
| Polyethylene glycol | PEG 400 | 58.5% | 58% |
| Thickening silica | Aerosil 200 | 1.5% | 2% |
| CMC | 9M31X | 40% | 40% |
| Brookfield Viscosity | After Preparation | 2200 cPs | 5360 cPs |
| | After 24 hrs aging | 2320 cPs | — |
| | After 4 wk. Aging | 1700 cPs | 5600 cPs |

Data of FPS 4-1 (Table 4-a) indicates that a high-solids (40 wt. %), stable and low-viscosity fluid polymer suspension of 9M31X CMC (available from Aqualon, Wilmington, Del.) could be prepared with 58.5 wt. % PEG 400 (available from Dow Chemical) and 1.5 wt. % Aerosil 200 silica (available from Degussa AG, Germany). Properties of FPS 4-2 highlight the thickening efficiency of Aerosil 200 silica; increasing the level of silica by ⅓, roughly, doubles the final viscosity of the suspension.

The following Examples further illustrate the usefulness and applicability of PEG based CMC FPS in a typical paper coating composition.

A generic paper coating formulation stock (Table 4-b) was prepared for application onto ground wood-free paper. Fractions of the formulation were individually thickened with either the PEG based CMC FPS of the present invention (FPS 4-1), Liberty 3794 product (a Mineral Oil based CMC FPS available from Aqualon) or with dry 7L2C CMC equivalent (standard low Mw paper grade CMC available from Aqualon). Sufficient polymer was added to achieve a target Brookfield viscosity of the paper coatings of approximately 1500-cPs.

TABLE 4-b

| Paper coating formulation (52% Total solids) | |
| --- | --- |
| Additive | Dosage |
| Delaminated clay | 90 parts |
| Calcined clay | 10 parts |
| SB latex | 5 parts |
| Dispersant | 0.15 parts |
| Optical brightener | 1 parts |

The dosages and measured properties of the formulations were listed in the following Table 4-c.

TABLE 4-c

Comparative wet coating and coated paper brightness data

| | | | | | Brightness | |
| --- | --- | --- | --- | --- | --- | --- |
| Thickener | Brkfd μ cPs | Dosage parts | GWR g | HHSV cPs | Uncal-endered | Cal-endered |
| PEG/9M31XF FPS (FPS 4-1) | 1450 | 0.60 | 104 | 30/26 | 78.0 | 80.8 |
| Liberty 3794 | 1400 | 0.47 | 78 | 38/30 | 76.9 | 79.3 |
| 7L2C CMC equivalent (dry) | 1500 | 2.20 | 127 | 50/42 | 77.6 | 79.8 |

Brkfd μ: RVT Brookfaeld viscosity at 100 rpm
Dosage: Parts thickener per 100 parts pigment
GWR: Gravimetric Water Retention as grams water lost in 1 minute test
HHSV: Hercules High Shear Viscosity at 2200 & 4,400 rpm, $2^{nd}$ pass, "E" bob.

The data assembled in Table 4-c indicates that on an as-is basis, the PEG based 9M31XF CMC suspension of FPS 4-1 offers a dosage efficiency standing between that of powdered CMC (7L2C, equivalent) and Liberty 3794 product, yet much more closely aligned with Liberty 3794 suspension. The dosage efficiency difference between both suspensions can be explained by the difference in the CMC active content (45% Vs 40%) in Liberty 3794 product and PEG suspension, respectively.

Water retention values (GWR) recorded for the PEG/9M31XF suspension were significantly improved over those generated for the powdered CMC. Also, the PEG suspension imparts desirable Hercules high shear behavior (HHSV). Lower high-shear viscosity can translate into improved coat weight control in many instances.

The three thickened coating samples were applied to free-sheet paper stock at approximately 9 lbs/3,000 ft$^2$. Brightness was measured with Diano S-4 calorimeter, both before and after supercalendering, for all paper samples. As per the statistical standard of 0.5 brightness units, it was surprisingly found that the paper coated with coating thickened with PEG/9M31XF FPS of the present invention was significantly brighter than Liberty 3794 and powdered CMC counterpart in both calendered and uncalendered states.

Example 5

The following CMC and Guar and Guar derivatives based FPS compositions as an additive to oilfield fluids illustrate the unexpected results of the present invention.

Data in Tables 5-a and 5-b illustrates the unexpected results of the present invention in functional systems with respect to the stability (Table 5-a) and extremely low oil and grease "hexane" extraction levels (Table 5-b) of the PEG FPS compositions.

It was surprisingly found that unlike the mineral oil suspensions, the PEG suspensions of the present invention did pass the EPA 1664 oil and grease test (Table 5-b) while providing high-solids, low-viscosity and stable suspensions to formulate drilling fluids, completion/workover fluids, oil-well cement slurries and hydraulic fracturing fluids for field operations (Table 5-a). While the PEG/CMc suspension FPS 5-1 can be used in both drilling fluids and completion/workover fluids, suspensions 5-2, 5-3 and 54 are better suitable for fracturing fluids.

TABLE 5-a

Suspensions for Oilfield applications

| Additive | FPS 5-1 | FPS 5-2 | FPS 5-3 | FPS 5-4 | FPS 5-5 | FPS 5-6 |
| --- | --- | --- | --- | --- | --- | --- |
| PEG 400 | 58.5% | 58% | 58% | 53.5% | 68% | — |
| PEG 200 | — | — | — | — | — | 68.8% |
| Aerosil 200 | 1.5% | 2% | 2% | 1.5% | 1.73% | 1.13% |
| 9H4XF CMC | 40% | — | — | — | — | — |
| Galactasol ® 476 (HPG)[1] | — | 40% | — | — | — | — |
| Galactasol ® 650 (CMHPG)[2] | — | — | 40% | 45% | — | — |
| PVA, Airvol 540-S[3] | — | — | — | — | 30.3% | — |
| Natrosol HIVIS | — | — | — | — | — | 30.08% |
| Brookfield Viscosity. cPs | | | | | | |
| After Preparation | 915 | 2200 | 1700 | 3320 | 1330 | 2540 |
| After 72 hrs aging | 1010 | 2620 | — | — | — | — |
| Flowing properties | | | | | | |
| After Preparation | 51 sec. | 139 sec. | 95 sec. | 228 sec. | — | — |
| After 72 hrs aging | 49 sec. | 53 sec. | — | — | — | — |

[1]: HydroxyPropyl Guar
[2]: CarboxyMethyl HydroxyPropyl Guar
[3]: Polyvinyl Alcohol, available from AirProducts,Allentown, PA, USA

TABLE 5-b

Oil & Grease test of Suspensions for Oilfield applications

| Substance | Oil & Grease (EPA 1664) | |
| --- | --- | --- |
| Ecolane 130* White Medicinal Oil | 75.07 wt. % | 750,700 mg/l |
| PEG 400 | 0.049 wt. % | 490 mg/l |
| 45 wt. % Guar suspension in Ecolane 130 | 10.99 wt. % | 109,900 mg/l |
| 40 wt. % CMHPG suspension in PEG400 (FPS 5-3) | 0.002 wt. % | 20 mg/l |

*Available from TOTAL Co., France

Example 6

Application in Drilling Fluids

The following Example further illustrates the usefulness and applicability of PEG based CMC or PAC FPS in typical oil well drilling fluid compositions.

higher apparent viscosity and significantly lower fluid loss. Despite a reduced amount of active content in the composition (0.88 ppb Vs 1.0 ppb), the PEG suspension of the present invention develops even improved properties over the AquaPAC® Reg precursor of composition 5, thanks to its fast dissolution.

TABLE 6-a

Rheology and fluid loss properties of a typical salt saturated Oil field drilling fluid
Prehydrated bentonite, 125 ppb NaCl, 10 ppb Rev-Dust, Polymer (pH ~ 9.0-9.5)

|  |  | Composition 3 | Composition 4 | Composition 5 | Composition 6 |
|---|---|---|---|---|---|
| Polymer | Type | Staflo Regular | AquaPAC Liquid | AquaPAC.Reg, #82985 | |
|  | Descritpion | Powder | Mineral oil FPS | Powder | PEG FPS (*) |
|  | Active content | 100% | 45% | 100% | 40% |
|  | Reference | X-32686-39-6 | L767 | 82985 | X-33342-67-1 |
|  | Concentration | 1.0 lb/bbl | 2.2 lb/bbl | 1.0 lb/bbl | 2.2 lb/bbl |
| Test temperature, °C. |  | 25.2 | 25.1 | 25.2 | 25 |
| Fann | 600 rpm | 24.5 | 25.0 | 30.5 | 37.5 |
| Rheology, | 300 rpm | 12 | 12.5 | 16.5 | 20.0 |
| DR | 200 rpm | 8.5 | 9.0 | 11.5 | 14.0 |
|  | 100 rpm | 5 | 5 | 7 | 8 |
|  | 60 rpm | 3 | 3.5 | 5 | 5.5 |
|  | 30 rpm | 2 | 2.5 | 3 | 3.5 |
|  | 6 rpm | 1 | 1 | 1 | 1.5 |
|  | 3 rpm | 1 | 1 | 1 | 1 |
| Apparent Viscosity, cPs |  | 12.25 | 12.50 | 15.25 | 18.75 |
| Plastic Viscosity, cPs |  | 12.5 | 12.50 | 14.00 | 17.50 |
| Yield Point, lb/100 ft$^2$ |  | −0.25 | 0 | 2.5 | 2.5 |
| 30' API Fluid Loss, ml |  | 21.6 | 18.1 | 12.6 | 11.4 |

(*): 40% suspension of AquaPAC Reg lot 82985 in PEG 400.

A typical oilfield drilling fluid composition including commercially available PACs and the associated FPS composition of this invention were prepared (Table 6-a). For comparative purposes, Staflo® Regular product (Composition 3) available from Akzo-Nobel (Amesfoort, the Netherlands) as well as a commercially available FPS (AquaPAC® Liquid available from Aqualon) using white medicinal oil as a base carrier (Composition 4) were included in the evaluation. The dry PAC materials were tested at 1.00 lb/bbl while the suspensions were tested at 2.2 lb/bbl.

The performance test is carried out in sodium chloride saturated drilling fluids containing 10 lb/bbl pre-hydrated Aquagel bentonite, 10 lb/bbl Rev-Dust and variable polymer concentrations. The Rev-dust is used to simulate the presence of cuttings in the drilling fluid during the drilling process. The PAC materials were evaluated on the basis of their contribution to the viscosity development and fluid loss reduction of the drilling fluid.

The test drilling fluid was prepared in a Hamilton Beach mixer (~11500 rpm) by adding 125 g sodium chloride into a mixing cup containing 356 g (350 ml) of pre-hydrated bentonite (10 lb/bbl) and mixing the resulting mixture for 5 minutes. Then, 10 g Rev-dust were added and the suspension was mixed for an additional 5 minutes. Then, the appropriate amount of PAC material was added and mixed for an elapsed time of 20 minutes. Measurement of both Fann apparent viscosity as well as fluid loss properties was then performed after 2 hours static ageing in a water bath at 25° C.

Data in Table 6-a indicates that polymers of Examples 6-a and 6-b, used in the composition it same active dosage, behave similarly while the suspension of 40 wt. % AquaPAC® Reg in PEG 400 (composition 6) develops much It can be seen from Table 6-a that the suspension of AquaPAC® Reg in PEG 400 (composition 6), subject of this invention, is an effective viscosifier and fluid loss reducer of oil well drilling fluids Application in Completion/Workover Fluids The following Example further illustrates the usefulness and applicability of PEG based HEC FPS in brines used as clear solids-free completion/workover fluid compositions.

Completion/workover fluids consist of a variety of brines of different salinity characterized by a density ranging from 8.5 lb/gal (pound per gallon) for seawater up to 19.2 lb/gal for heavy brines containing zinc and calcium bromide salts. While high viscosity HEC, such as Natrosol® HIVIS available from Aqualon, is widely as a standard thickener for such brines because of its non-ionic character, Xanthan gum is also used especially in low density and non-calcium based brines to provide particular rheology characteristics to optimize the fluid carrying capacity and gel strength properties.

The thickening efficiency of Natrosol® HIVIS HEC based PEG FPS (FPS 5-6) was evaluated against its precursor by dissolving 1.5 lb/bbl equivalent dry HEC in NaCl saturated brine. The NaCl saturated brine was first prepared by dissolving 360 g NaCl in 1000 ml Deionized water. Then, 1.5 g dry HEC or 5.0 g HEC FPS (30% active content) were added into 420 g NaCl saturated water while mixing on Hamilton beach mixer (~11,500 rpm). To speed up the dissolution of the polymer, 1 g MgO was added into the solution to raise the pH to 9-10 range). To reduce/eliminate excess foaming, a few drops of defoamer were added. The solution was mixed for an elapsed time of 60 minutes. Measurement of both Fann rheology as well as fluid loss properties was then performed after 4 hours static ageing in a water bath at 25° C.

Data in Table 6-b indicates that both the PEG/HIVIS HEC suspension (FPS 5-6) and its dry precursor used in the NaCl saturated water at same active dosage, behave similarly in terms of both rheology and filtration control properties.

TABLE 6-b

Rheology and fluid loss properties of a typical NaCl saturated brine

| | | Composition 7 | Composition 8 |
|---|---|---|---|
| Polymer | Type | Natrosol HIVIS | HIVIS suspension |
| | Description | Powder | FPS 5-6* |
| | Active content | 100% | 30.08% |
| | Reference | #21487 | X-33660-71-3C |
| | Concentration | 1.5 lb/bbl | 5.0 lb/bbl |
| Test temperature, ° C. | | 25 | 25 |
| Fann | 600 rpm | 64.5 | 67.0 |
| Rheology, | 300 rpm | 44.5 | 48.0 |
| DR | 200 rpm | 35.5 | 38.5 |
| | 100 rpm | 23.5 | 26.0 |
| | 60 rpm | 16.5 | 19.5 |
| | 30 rpm | 10 | 12.5 |
| | 6 rpm | 3.5 | 4.0 |
| | 3 rpm | 2.5 | 3.0 |
| Apparent Viscosity, cPs | | 32.25 | 33.5 |
| Plastic Viscosity, cPs | | 20 | 19.0 |
| Yield Point, lb/100 ft$^2$ | | 24.5 | 29.0 |
| 30' API Fluid Loss, ml | | 19.5 | 17.1 |
| pH | | 10.5 | 10.1 |

(*): 30.08% suspension of Natrosol HIVIS lot 21487 in PEG 200- Suspension remains pourable and stable for at least 2 hours.

It can be seen from Table 6-b that the suspension of Natrosol® HIVIS in PEG 200, subject of this invention, is an effective viscosifier and fluid loss reducer of completion/workover fluids.

Application in Oil-Well Cement Slurries

Oil well cementing is the process of mixing a slurry of cement, water and various additives and pumping it down through a steel casing to critical points in the annular space between the formation and the casing. To ensure a good cementing job operation, the cement slurry needs to be stable and easy to pump/handle. Among all other properties, fluid loss control is a key in designing cement slurries, because it conditions the overall cement characteristics. Fluid loss control additives (FLAC), are therefore required to prevent the cement slurry dehydration in the annulus due to permeable zones and maintaining the integrity of the cement slurry.

A variety of fluid loss additives is used in oil-well cementing to cover a wide range of operating conditions that are typically encountered down-hole, such as salt and high temperature environments. The—so called—low temperature segment covers operating conditions ranging from ambient temperature up to about 180° F. In this segment, PVA and HEC are the most dominant fluid loss additives used to control filtration properties. Moderate temperature segment ranges from 180 to 250° F. Despite the fact that HEC use can be extended up to 220° F., the most dominant FLACs for these conditions are synthetics in nature. For temperatures exceeding 250° F., AMPS based synthetic FLACs are the only ones effective to sufficiently control the fluid loss control properties.

The following example illustrates the typical performance of FLACs, particularly PEG based PVA of the present invention (FPS 5-5), in a low temperature oil-well cement slurry composition.

The slurries were formulated using additives and mixing/formulation techniques commonly employed in the industry as recommended by the American Petroleum Institute (API). All concentrations of additives in the slurry compositions 9 & 10 are based on weight of cement (bwoc).

The oil well cement slurry was prepared by adding the cement dry mixture into the mix-water, eventually, containing the FLAC. The dry mixture consists of 600 g Lonestar cement "H", 1.2 g dispersant (0.20 wt. % bwoc Lomar D) and, eventually, 3 g PVA (0.50 wt % bwoc Airvol 540-S, available from Air Products, Allentown, Pa., USA). For the comparative experiment with PEG based PVA FPS (FPS 5-5), the polymer suspension was added into the mix-water prior to adding the dry mixture. In both preparations, a few drops of defoamer were added to reduce excessive foaming of the cement slurry.

The performance testing of the oil-well cement slurries were conducted in terms of rheology and fluid loss control properties at relatively low temperature. Typically, the "mixing rheology" was measured with Fann type viscometer just after the slurry preparation at room temperature (~80° F.), to simulate the mixing and pumping at the surface, while the "API rheology" was measured after conditioning the slurry at 80° F. for 20 minutes. The fluid loss control properties were measured at 80° F. after the slurry conditioning.

Data in Table 6-c shows that PEG based PVA FPS provides excellent fluid loss control properties, slightly better than the precursor, and much better mixing rheology. In fact, the yield value of the control slurry (composition 9) prepared with dry PVA is about double the value of the cement slurry (composition 10) made with the PEG based PVA FPS (FPS 5-5), subject of this invention. Practically, the high yield value would require more energy to pump and place the cement slurry down the hole.

TABLE 6-c

Functionality of PVA FPS as a Fluid Loss additive in oiwell cement slurries

| | Composition 9 | | Composition 10 | |
|---|---|---|---|---|
| Ingredients | g | bwcc | g | bwcc |
| Cement Lonestar H | 600 | — | 600 | — |
| LOMAR D | 1.2 | 0.20% | 1.2 | 0.20% |
| AIRVOL 540-S dry. #01050240L | 3 | 0.5% | — | — |
| PEG/AIRVOL 540-S FPS (FPS 5-5) | — | — | 10.02 | 1.67% |
| Anti-foam | few drops | | few drops | |
| Demi-water | 228 | 38.0% | 220.8 | 36.8% |
| Fann Type Rheology | Mixing Rheology | API Rheology | Mixing Rheology | API Rheology |
| Conditionning | Before Conditionning | After Conditionning | Before Conditionning | After Conditionning |
| Test Temperature | 80° F. | 80° F. | | |
| 300-rpm DR | 226 | 215 | 227 | 193 |
| 200-rpm DR | 163 | 146 | 159 | 131 |
| 100-rpm DR | 99 | 75 | 87 | 70.5 |

TABLE 6-c-continued

Functionality of PVA FPS as a Fluid Loss additive in oiwell cement slurries

| Ingredients | Composition 9 | | Composition 10 | |
|---|---|---|---|---|
| | g | bwcc | g | bwcc |
| 60-rpm DR 73.5 | 46 | 56 | 46.5 | |
| 30-rpm DR | 58 | 23.5 | 32.5 | 27 |
| 6-rpm DR | 36 | 6.5 | 13 | 12 |
| 3-rpm DR | 27 | 4 | 11 | 10 |
| P.V. (1.5xFx(300 DR − 100 DR), cPs | 190.5 | 210 | 210 | 183.75 |
| Yv (Fx300 DR − PV), lb/100 ft$^2$ | 35.5 | 5 | 17 | 9.25 |
| Filtrate collected under 1000 psi | Static Fluid Loss Cell | | | |
| Test Temperature | 80° F. | | 80° F. | |
| 30° API Fluid Loss. cc | 16.4 | | 12.0 | |

It can be seen from Table 6-c that the suspension of PVA in PEG 400, subject of this invention, is an effective fluid loss control additive of oil-well cement slurries.

The use application example of PVA suspension in PVA in oil-well cement slurries is given for illustration puporses only. It should, in any case, not limit the invention to PVA only. As illustrated earlier, suspensions of HEC in PEG can also be prepared, and may as well be used as FLACs or suspending agents, depending upon their Mw.

Example 7

The following Example further illustrates the usefulness and applicability of PEG based CMC FPS in a typical civil engineering drilling fluids.

A typical civil-engineering drilling fluid composition including commercially available CMCs and corresponding FPS compositions of this invention were prepared (Table 7). For comparative purposes, AquaVIS 633 CMC (composition 12) and its FPS version (Polymer SC50, composition 13), both available from Aqualon were included in the evaluation. Both the dry CMC and the corresponding FPS were used on an as-is basis at 0.40 g/l (1.0% based on weight of bentonite in the mud composition).

TABLE 7

Rheology and fluid loss properties of a typical Civil-EngIneering drillIng fluid
D.I. water, 40 g/l C2T bentonite & 0.40 g/l Polymer

| | | Composition 11 | Composition 12 | Composition 13 | Composition 14 |
|---|---|---|---|---|---|
| Bentonite | Type | C2T from Sud-Chemie, France | | | |
| | Concentration | 40 g/l in D.I. Water | | | |
| Polymer | Type | None | AquaVIS633 | Polymer SC50 | 9H4XF |
| | Descritpion | — | Powder | Mineral oil FPS | PEG 400 FPS |
| | Active content | — | 100% | 45% | 40% |
| | Reference | — | 10819 | L767 | FPS 5-1 |
| | Concentration | 0 | 0.40 g/l | 0.40 g/l | 0.40 g/l |
| pH | | 10.21 | 10.23 | 10.18 | 10.2 |
| Test temperature, ° C. | | 25.6 | 26 | 25.6 | 25.6 |
| Fann | 600 rpm | 28.5 | 48.0 | 35.5 | 36.0 |
| Rheology, | 300 rpm | 20.0 | 34.0 | 25.0 | 25.0 |
| DR | 200 rpm | 16.0 | 28.0 | 20.5 | 20.5 |
| | 100 rpm | 12 | 21 | 15 | 15 |
| | 60 rpm | 10 | 17.5 | 12 | 12.5 |
| | 30 rpm | 8 | 13.5 | 9.5 | 10 |
| | 6 rpm | 5.5 | 8.5 | 6 | 6.5 |
| | 3 rpm | 5 | 7.5 | 5.5 | 6 |
| Apparent Viscosity, cPs | | 14.25 | 24.00 | 17.75 | 18.00 |
| Plastic Viscosity, cPs | | 8.50 | 14.00 | 10.50 | 11.00 |
| Yield Point, lb/100 ft$^2$ | | 11.5 | 20 | 14.5 | 14 |
| Marsh Funnel Viscosity, sec. | | 36 | 47 | 40 | 42 |
| Fluid Loss, ml | @7.5 minutes | 8.5 | 6.6 | 6.8 | 7.8 |
| | @30 minutes | 18.1 | 14.3 | 17.8 | 16.2 |

It was surprisingly found that, despite its lower active content (40% Vs 45% for the commercial Polymer SC50 FPS), the PEG suspension of the present invention (composition 14) prepared with 9H4XF CMC (available from is Aqualon) performs at least as good as the commercial FPS reference (composition 13). The PEG/9H4X CMC suspension develops comparative Fann rheology and better fluid loss control properties and higher Marsh Funnel viscosity than the commercial reference. Because of its fast dissolution, the PEG suspension of this invention develops outstanding properties at 0.4 wt. % active polymer dosage (based on weight of bentonite) versus 1.0 wt. % for the dry CMC of composition 12.

It can be seen from Table 7 that the suspension of 9H4XF CMC in PEG 400, subject of this invention, is an effective viscosifier and fluid loss reducer for Civil-engineering applications, including tunneling, trenching, diaphragm walling, pilling, horizontal drilling and water-well drilling. For trenching applications, Guar based PEG FPSs of Table 5-a (FPS 5-2 to 54) are more preferred for economical reasons. They are used on-site either to prepare a solution (polymer based solids-free fluids) or in combination with bentonite. For water-well drilling applications, both Guar and CMC based PEG FPSs are preferably used as solids-free solutions to minimize the contamination of the aquifers.

Example 8

This Example illustrates an HEC based FPS composition of the present invention useful in joint compounds. This example is given for illustration purposes only. It should, in any case, not limit the invention to joint compounds only. As illustrated earlier, suspensions of other WSPs in PEG can also be prepared, and may as well be useful in other construction/building compositions.

Samples of PEG based HEC and its dry precursor (Natrosol 250 HHBR (30% active), available from Hercules Inc., Wilmington, Del.) were evaluated in a typical all purpose heavy weight joint compound variety (Table 8-a). The thickener was added into the joint compound composition it 0.4 wt % active.

TABLE 8-a

Joint Compound composition

| Ingredients | Content, g | |
|---|---|---|
| Water | 243 | 235.5 |
| Troysan 174 (Biocide) | 0.4 | 0.4 |
| Reichl 40104 (Latex) | 20 | 20 |
| Geo white #9 (CaCO3) | 500 | 500 |
| Gel B (Attapulgite) | 13.3 | 13.3 |
| 4-K mica | 20 | 20 |
| Natrosol HHBR, #35851 | 3.2 | — |
| PEG/HHBR suspension (30% active) | — | 10.7 |

Data in Table 8-b indicates that the PEG based Natrosol 250 HHBR behaves similarly to its dry precursor. Both joint compounds compositions trowel basically the same. After 48 hour aging, the properties such as eliminating pocks, wet edge, etc., remain still equivalent. Both JCs have essentially identical properties.

TABLE 8-b

Joint Compound properties

| Thickener | Ease of Mixing | Creamy Appearance | JC Brabender Units | | Bulk density |
|---|---|---|---|---|---|
| | | | Initial | 24 hours | |
| Natrosol HHBR, #35851 | 3.5 | 1.5 minutes | 480 BU | 440 BU | 14.2 ppg |
| PEG/HHBR suspension (30% active) | 3.5 | 1.5 minutes | 495 BU | 520 BU | 14.2 ppg |

Example 9

This Example illustrates a CMC based FPS composition of the present invention useful in Ceramics formulations.

The FPS composition in Table 9-a illustrates the unexpected low viscosity and outstanding long-term stability of the present invention for use in ceramic bodies and ceramic glazes.

TABLE 9-a

Suspensions for Ceramics applications

| Additive | FPS 9 |
|---|---|
| PEG 400 | 58.5% |
| Aerosil 200 | 1.5% |
| 7MXF CMC | 40% |
| Brookfield Viscosity | |
| After Preparation | 1320 cPs |
| After 72 hrs aging | 1360 cPs |
| After 10 days aging | 1440 cPs |
| Physical stability after 7 months storage | <7% phase separation |

Application in Ceramic Body

When the PEG/CMC suspension (FPS 9) of the present invention is used in a ceramic body composition (Table 9-b), it is expected to provide the properties listed in the Table 9-c TABLE 9-b Use Application of PEG/CMC FPS in Ceramic Body

| Composition | Content, wt.% |
|---|---|
| Feldspar | 60-70 |
| Clay | 20-30 |
| Quartz | 5-7 |
| Others | 1-5 |
| Water reducing-agent | 0.3-0.5 |
| PEG based 7MXF CMC (FPS 9) | 0.05-0.20 |

TABLE 9-c

Properties of a ceramic body composition

| | Properties |
|---|---|
| Solids content | 65-70% |
| Density | 1.5-1.7 g/ml |
| Flow velocity | 30-55 seconds |
| Residue (75 μm) | 0.10-0.50% |

Application in Ceramic Glaze

When the PEG/CMC suspension (FPS 9) of the present invention is used in a ceramic glaze composition (Table 9-d), it is expected to provide the properties listed in the Table 9-e TABLE 9-d Use Application of PEGICMC FPS in Ceramic Glaze

| Composition | Content, wt. % |
|---|---|
| Ceramic frit | 93-95 |
| Kaolin | 5-7 |
| S.T.P.P. | 0.20-0.35% |
| PEG based 7MXF CMC (FPS 9) | 0.10-0.50% |

TABLE 9-e

Properties of a ceramic glaze composition

| | Properties |
|---|---|
| Solids content | 65-70 % |
| Density | 1.85-1.95 g/ml |
| Flow velocity | 55-65 seconds |
| Residue (75 μm) | 0.10-0.30% |

Example 10

This Example illustrates a CMC based FPS composition of the present invention useful in mineral processing.

When PEG/CMC suspension (FPS 9 in Table 9-a) of the present invention is used in a mineral processing suspension of crude ores containing talc and/or pyrophyllite, it is expected that the FPS performance would results in keeping the slime minerals in a wetted and non-floatable state, by adsorbing onto their particle surfaces and converting the slimes into forms that are easily wetted and separated. The FPS is used at concentrations varying from 0.1 lb./ton to 2.0 lbs./ton of dry ore.

While this invention has been described with respect to specific embodiments, it should be understood that these embodiments are not intended to be limiting and that many variations and modifications are possible without departing from the scope and spirit of this invention.

What is claimed:

1. A composition consisting of
   (a) an aqueous based functional system selected from the group consisting of personal care products, household care, oil field servicing fluids, civil engineering servicing fluids, paper coatings, construction fluids, ceramic glazes, foods, firefighting retardants, mineral processing, and aqueous based coatings wherein the aqueous based functional system excludes oral care products and
   (b) a stable fluid polymer suspension (FPS) thickening agent consisting of
      i) a polysaccharide,
      ii) polyethylene glycol, and
      iii) hydrated thickening silica.

2. The composition of claim 1, wherein the upper limit of the amount of the polysaccharide based on the total weight of the FPS is 60 wt %.

3. The composition of claim 1, wherein the upper limit of the amount of the polysaccharide based on the total weight of the FPS is 50 wt %.

4. The composition of claim 1, wherein the upper limit of the amount of the polysaccharide based on the total weight of the FPS is 40 wt %.

5. The composition of claim 1, wherein the lower limit of the amount of the polysaccharide based on the total weight of the FPS is 10 wt %.

6. The composition of claim 1, wherein the lower limit of the amount of the polysaccharide based on the total weight of the FPS is 20 wt %.

7. The composition of claim 1, wherein the lower limit of the amount of the polysaccharide based on the total weight of the FPS is 30 wt %.

8. The composition of claim 1, wherein the upper limit of the amount of the polyethylene glycol based on the total weight of the FPS is 90 wt %.

9. The composition of claim 1, wherein the upper limit of the amount of the polyethylene glycol based on the total weight of the FPS is 80 wt %.

10. The composition of claim 1, wherein the upper limit of the amount of the polyethylene glycol based on the total weight of the FPS is 70 wt %.

11. The composition of claim 1, wherein the lower limit of the amount of the polyethylene glycol based on the total weight of the FPS is 40 wt %.

12. The composition of claim 1, wherein the lower limit of the amount of the polyethylene glycol based on the total weight of the FPS is 50 wt %.

13. The composition of claim 1, wherein the lower limit of the amount of the polyethylene glycol based on the total weight of the FPS is 60 wt %.

14. The composition of claim 1, wherein the upper limit of the amount of the hydrated thickening silica based on the total weight of the FPS is 3.0 wt %.

15. The composition of claim 1, wherein the upper limit of the amount of the hydrated thickening silica based on the total weight of the FPS is 2.0 wt %.

16. The composition of claim 1, wherein the lower limit of the amount of the hydrated thickening silica based on the total weight of the FPS is 0.1 wt %.

17. The composition of claim 1, wherein the lower limit of the amount of the hydrated thickening silica based on the total weight of the FPS is 0.5 wt %.

18. The composition of claim 1, wherein the polysaccharide is selected from the group consisting of hydroxyethylcellulose (HEC), carboxymethylcellulose (CMC), polyanionic cellulose (PAC), carboxymethyl hydroxyethyl cellulose (CMHEC), and methyl cellulose (MC).

19. The composition of claim 1, wherein the polysaccharide is selected from the group consisting of wellan gum and xanthan gum.

20. The composition of claim 1, wherein the polysaccharide is selected from the group consisting of hydroxyethyl guar (HEG), hydroxypropyl guar (HPG), carboxymethyl hydroxypropyl guar (CMHPG) and carboxymethyl guar (CMG).

21. The composition of claim 1, wherein the polyethylene glycol is environmentally friendly, is approved by the FDA for use in food contact, is biodegradable, has a melting point as low as −50° C., and has molar mass higher than about 200 grams per mol.

22. The composition of claim 1, wherein the hydrated thickening silica is a fumed silica that has a small particle size of about 10 μm and a large surface area of from about 200 to 300 square meters per gram.

23. The composition of claim 1, wherein the functional system is personal care product that is selected from the group consisting of hair care, skin care, and sunscreen care products.

24. The composition of claim 1, wherein the functional system is household care composition that is selected from the group consisting of laundry detergent, dish washing products, heavy duty cleaning products, machinery lubricating products, disinfecting products, and fabric enhancing products.

25. The composition of claim 1, wherein the functional system is water based protective coatings compositions selected from the group of latex paints.

26. The composition of claim 1, wherein the functional system is a paper coating and paper making composition.

27. The composition of claim 1, wherein the functional system is oilfield servicing fluid compositions.

28. The composition of claim 27, wherein the oil field servicing fluids compositions are selected from the group consisting of drilling fluids, completion/workover fluids, fracturing fluids and oil well cement fluids.

29. The composition of claim 1, wherein the functional system is civil engineering servicing fluid compositions used in applications including tunneling, diaphragm walling, pilling, trenching, horizontal drilling and water well drilling.

30. The composition of claim 1, wherein the functional system is construction/building compositions selected from the group consisting of concrete, tile cement, adhesives, projection plasters, stuccos based on cement and synthetic binders, ready mixed mortars, manually applied mortars, underwater concrete, joint cement, joint compounds, gypsum board, crack fillers, floor screeds, and adhesive mortars.

31. The composition of claim 1, wherein the functional system is a ceramic body or glaze.

32. The composition of claim 1, wherein the functional system is food selected from the group consisting of tortillas, cake mixes, bread mixes, bread, ice cream, sour cream, pasteurized processed cheese spreads, and cheese foods, instant cold and hot drinks, ready to drink beverages, and fruit flavored drinks and food packaging.

33. The composition of claim 1, wherein the functional system is firefighting retardants and mining and metal processing.

34. A process of thickening an aqueous based functional system selected from the group consisting of personal care products, household care, oil field servicing fluids, civil engineering servicing fluids, paper coatings, construction fluids, ceramic glazes, foods, firefighting retardants, mineral processing, and water based protective coatings wherein the aqueous based functional system excludes oral care products, consisting of adding and mixing a sufficient amount of a stable fluid polymer suspension that is compatible with the aqueous based functional system to thicken the functional system wherein the stable fluid polymer suspension consisting of a polysaccharide, polyethylene glycol, and hydrated thickening silica.

35. The composition of claim 1, wherein the polysaccharide is guar.

36. The composition of claim 35, wherein the guar is cationic guar.

37. The process of claim 34, wherein the upper limit of the amount of the polysaccharide based on the total weight of the FPS is 60 wt %.

38. The process of claim 34, wherein the upper limit of the amount of the polysaccharide based on the total weight of the FPS is 50 wt %.

39. The process of claim 34, wherein the upper limit of the amount of the polysaccharide based on the total weight of the FPS is 40 wt %.

40. The process of claim 34, wherein the lower limit of the amount of the polysaccharide based on the total weight of the FPS is 10 wt %.

41. The process of claim 34, wherein the lower limit of the amount of the polysaccharide based on the total weight of the FPS is 20 wt %.

42. The process of claim 34, wherein the lower limit of the amount of the polysaccharide based on the total weight of the FPS is 30 wt %.

43. The process of claim 34, wherein the upper limit of the amount of the polyethylene glycol based on the total weight of the FPS is 90 wt %.

44. The process of claim 34, wherein the upper limit of the amount of the polyethylene glycol based on the total weight of the FPS is 80 wt %.

45. The process of claim 34, wherein the upper limit of the amount of the polyethylene glycol based on the total weight of the FPS is 70 wt %.

46. The process of claim 34, wherein the lower limit of the amount of the polyethylene glycol based on the total weight of the FPS is 40 wt %.

47. The process of claim 34, wherein the lower limit of the amount of the polyethylene glycol based on the total weight of the FPS is 50 wt %.

48. The process of claim 34, wherein the lower limit of the amount of the polyethylene glycol based on the total weight of the FPS is 60 wt %.

49. The process of claim 34, wherein the upper limit of the amount of the hydrated thickening silica based on the total weight of the FPS is 3.0 wt %.

50. The process of claim 34, wherein the upper limit of the amount of the hydrated thickening silica based on the total weight of the FPS is 2.0 wt %.

51. The process of claim 34, wherein the lower limit of the amount of the hydrated thickening silica based on the total weight of the FPS is 0.1 wt %.

52. The process of claim 34, wherein the lower limit of the amount of the hydrated thickening silica based on the total weight of the FPS is 0.5 wt %.

53. The process of claim 34, wherein the polysaccharide is selected from the group consisting of hydroxyethylcellulose (HEC), carboxymethylcellulose (CMC), carboxymethyl hydroxyethyl cellulose (CMHEC), polyanionic cellulose (PAC), methyl cellulose, (MC), and MC derivatives.

54. The process of claim 34, wherein the polysaccharide is selected from the group consisting of wellan gum and xanthan gum.

55. The process of claim 34, wherein the selected from the group consisting of hydroxyethyl guar (HEG), hydroxypropyl guar (HPG), carboxymethyl hydroxypropyl guar (CM-HPG) and carboxymethyl guar (CMG).

56. The process of claim 34, wherein the polyethylene glycol is environmentally friendly, is approved by the FDA for use in food contact, is biodegradable, has a melting point as low as −50° C., and has molar mass higher than about 200 grams per mole.

57. The process of claim 34, wherein the hydrated thickening silica is a fumed silica that has a small particle size of about 10 μm and a large surface area of from about 200 to 300 square meters per gram.

58. The process of claim 34, wherein the functional system is personal care product that is selected from the group consisting of hair care, skin care, and sunscreen care products.

59. The process of claim 34, wherein the functional system is household care composition that is selected from the group consisting of laundry detergent, dish washing products, heavy duty cleaning products, machinery lubricating products, disinfecting products, and fabric enhancing products.

60. The process of claim 34, wherein the functional system is water based protective coating compositions selected from the group of latex paints.

61. The process of claim 34, wherein the functional system is a paper coating and paper making composition.

62. The process of claim 34, wherein the functional system is oilfield servicing fluid compositions.

63. The process of claim 34, wherein the oil field servicing fluids compositions are selected from the group consisting of drilling fluids, completion/workover fluids, fracturing fluids and oil well cement fluids.

64. The process of claim 34, wherein the functional system is Civil Engineering servicing fluid compositions used in applications including tunneling, diaphragm walling, pilling, trenching, horizontal drilling and water well drilling.

65. The process of claim 34, wherein the functional system is construction/building compositions selected from the group consisting of concrete, tile cement, adhesives, projection plasters, stuccos based on cement and synthetic binders, ready mixed mortars, manually applied mortars, underwater concrete, joint cement, joint compounds, gypsum board, crack fillers, floor screeds, and adhesive mortars.

66. The process of claim 34, wherein the functional system is a ceramic body or glaze.

67. The process of claim 34, wherein the functional system is food selected from the group consisting of tortillas, cake mixes, bread mixes, bread, ice cream, sour cream, pasteurized processed cheese spreads, and cheese foods, instant cold and hot drinks, ready to drink beverages, and fruit flavored drinks and food packaging.

68. The process of claim 34, wherein the functional system is firefighting retardants and mining and metal processing.

69. The process of claim 34, wherein the polysaccharide is guar.

70. The process of claim 34, wherein the polysaccharide is cationic guar.

* * * * *